United States Patent
Freeman (10) Patent No.: US 12,389,954 B2
(45) Date of Patent: Aug. 19, 2025

(54) CHEST BINDER

(71) Applicant: For Them, Inc., New York, NY (US)

(72) Inventor: Chloe Freeman, New York, NY (US)

(73) Assignee: For Them, Inc., New York, NY (US)

( * ) Notice: Subject to any disclaimer, the term of this patent is extended or adjusted under 35 U.S.C. 154(b) by 0 days.

(21) Appl. No.: 18/706,733

(22) PCT Filed: Nov. 2, 2022

(86) PCT No.: PCT/US2022/048747
§ 371 (c)(1),
(2) Date: May 1, 2024

(87) PCT Pub. No.: WO2023/081238
PCT Pub. Date: May 11, 2023

(65) Prior Publication Data
US 2025/0040625 A1    Feb. 6, 2025

Related U.S. Application Data

(60) Provisional application No. 63/276,434, filed on Nov. 5, 2021.

(51) Int. Cl.
*A41C 1/02* (2006.01)
*A41C 3/00* (2006.01)

(52) U.S. Cl.
CPC ............... *A41C 1/02* (2013.01); *A41C 3/005* (2013.01)

(58) Field of Classification Search
CPC ...... A61F 13/145; A61F 5/03; A41B 2400/38; A41D 2400/38
USPC .......................................... 450/2, 3, 122, 123
See application file for complete search history.

(56) References Cited

U.S. PATENT DOCUMENTS

| | | | | | |
|---|---|---|---|---|---|
| 2,662,522 | A | * | 12/1953 | Muller | A61F 13/143 602/61 |
| 3,008,468 | A | * | 11/1961 | Williams | A41C 3/00 450/86 |
| 3,189,028 | A | * | 6/1965 | Dormire | A41C 3/06 602/61 |
| 3,194,234 | A | * | 7/1965 | Duckman | A61F 13/148 602/61 |
| 3,718,143 | A | * | 2/1973 | Pagano | A41C 3/00 450/75 |
| 4,217,905 | A | * | 8/1980 | Atwater | A41C 3/0057 450/74 |
| 4,289,137 | A | * | 9/1981 | Dell | A41C 3/02 2/912 |

(Continued)

OTHER PUBLICATIONS

International Search Report and Written Opinion, dated Feb. 16, 2023, for International Application No. PCT/US22/48747, 11 pages.

*Primary Examiner* — Jocelyn Bravo
(74) *Attorney, Agent, or Firm* — MASCHOFF BRENNAN; Benjamin Charkow (57) ABSTRACT

A 180-degree rotatable chest binder for compressing, flattening and stabilizing the breasts of the wearer. The chest binder is constructed of inner and outer layers, each made of four panels, joined together along the neck opening, arm openings and bottom openings of the wearer. This design permits the inner and outer layers to move independently, serving the two different functions of moving with the body for comfort while also compressing the chest.

10 Claims, 3 Drawing Sheets

(56) References Cited

U.S. PATENT DOCUMENTS

| | | | |
|---|---|---|---|
| 4,816,005 A * | 3/1989 | Braaten | A41C 3/02 450/74 |
| 5,060,648 A * | 10/1991 | Zarkesh | A61F 13/145 604/113 |
| 5,427,563 A * | 6/1995 | Manning | A61F 7/02 450/23 |
| 5,968,003 A * | 10/1999 | Sisson | A61F 13/145 602/53 |
| 6,099,382 A * | 8/2000 | Wilson | A41C 3/0057 2/247 |
| 6,165,045 A * | 12/2000 | Miller | A41C 3/0057 450/17 |
| 7,160,262 B2 * | 1/2007 | Wicks | A41C 1/08 602/76 |
| 8,465,341 B2 * | 6/2013 | Shashy | A41C 3/0057 450/39 |
| 9,480,288 B2 * | 11/2016 | Shashy | A41C 3/02 |
| 10,278,431 B2 | 5/2019 | McClean | |
| 11,284,648 B2 * | 3/2022 | Carlino | A41C 3/0085 |
| 11,350,679 B2 * | 6/2022 | Frankenbach | A41C 3/0014 |
| 2002/0022433 A1 * | 2/2002 | Yeung | A41C 3/0057 450/93 |
| 2004/0002288 A1 * | 1/2004 | Bell | A41C 3/0064 450/75 |
| 2011/0275276 A1 * | 11/2011 | Shashy | A41C 3/0057 450/86 |
| 2011/0275278 A1 * | 11/2011 | Shashy | A41C 3/0057 450/86 |
| 2012/0045967 A1 * | 2/2012 | Punsal | A41C 3/0057 450/82 |
| 2012/0244782 A1 * | 9/2012 | Pundyk | A41C 3/0057 450/70 |
| 2013/0084777 A1 | 4/2013 | Starr et al. | |
| 2016/0374405 A1 * | 12/2016 | Washington | A41C 1/02 450/76 |
| 2017/0055595 A1 * | 3/2017 | Zachi | A41C 3/0057 |
| 2019/0174841 A1 * | 6/2019 | Bastug | A41C 3/0007 |
| 2019/0231605 A1 * | 8/2019 | Lipshaw | A61F 5/02 |
| 2020/0205485 A1 * | 7/2020 | Frankenbach | A41C 3/005 |
| 2023/0088253 A1 * | 3/2023 | Guo | A41C 1/02 450/115 |
| 2023/0380517 A1 * | 11/2023 | Wu | A41C 1/12 |

* cited by examiner

CHEST BINDER

FIELD OF THE INVENTION

The present invention relates generally to a chest binder and more particularly to a 180-degree rotatable chest binder that compresses (to its maximum possible point), flattens and stabilizes the breasts of the wearer.

BACKGROUND OF THE INVENTION

Gender dysphoria is described by the Mayo Clinic as the feeling of discomfort or distress that occurs in people whose gender identity differs from their sex assigned at birth or sex-related physical characteristics. For some people, this dysphoria can be crippling and impair many aspects of day-to-day life. A chest binder helps to quell gender dysphoric feelings in those that are assigned female at birth but who gender identify with any other gender by minimizing the protrusion of the wearer's breasts for a flatter appearance.

A chest binder can support mental health, chest dysphoria and social dysphoria, and so is often worn daily by those in need of such a device. Traditional chest binder design to date has comprised a combination of mesh material, non-stretch and stretch fabric. Unfortunately, because of the use of non-stretch materials in combination with the tension applied from the mesh, the traditional chest binder often puts significant pressure on the chest, ribcage, shoulders and back of the wearer and can inhibit deep breathing, mobility and perspiration associated with physical exertion.

According to a 2017 study from the National Library of Medicine 97.2% of people wearing chest binders reported at least one negative outcome related to chest binding, including back pain, chest pain, poor posture, shoulder pain, shortness of breath and tissue changes.

Given that chest binders designed to date are often uncomfortable because of the compression forces exerted on various parts of the body, including the chest, ribcage, shoulders and back of the wearer, there exists a need to improve the design of a chest binder so that it serves its function of maximum compression and flattening of the breast tissue while being safe and comfortable, without the negative side effects experienced from chest binders to date.

SUMMARY OF THE INVENTION

A multi-paneled chest binder comprising an inner layer and an outer layer is provided. The chest binder consists of a front panel, rear panel, and side panels connecting the front and rear panels along the side panel longitudinal edges, with each of the respective panels comprising an inner and outer layer (also referred to as a panel).

These eight panels are defined as set forth in Table 1 below:

TABLE 1

| Identification of Chest Binder Panels | |
| --- | --- |
| Inner Front Panel | First Panel |
| Inner Rear Panel | Second Panel |
| Inner Left Side Panel | Third Panel |
| Inner Right Side Panel | Fourth Panel |
| Outer Front Panel | Fifth Panel |
| Outer Rear Panel | Sixth Panel |
| Outer Left Side Panel | Seventh Panel |
| Outer Right Side Panel | Eighth Panel |

The panels of the chest binder made in accordance with the present invention can be constructed out of any type of stretchable fabric. In embodiments, elastic runs along one or more of the arm openings and neck opening of the chest binder. The outer front panel and the inner front panel may be referred to collectively as the front panel. The outer rear panel and the inner rear panel may be referred to collectively as the rear panel. The outer left side panel and the inner left side panel may be referred to collectively as the left side panel. The outer right side panel and the inner right side panel may be referred to collectively as the right side panel.

In embodiments, the front and rear panels of the chest binder each contain a torso panel and right and left shoulder portions configured to extend over the right and left shoulders of the wearer. The right and left shoulder portions are spaced from each other and extend from the torso panel to define a portion of the neck opening. The front and rear right shoulder portions are joined at their edges (i.e., at a shoulder seam) to form a strap configured to extend over the right shoulder and the front and rear left shoulder portions are joined at their edges to form a strap configured to extend over the left shoulder, defining the neck opening. The torso panels and right and left shoulder portions of the various inner and outer panels are defined as set forth in Table 2 below:

TABLE 2

| Identification of Torso Panels and Shoulder Portions | | |
| --- | --- | --- |
| Panel | Item | Description |
| Inner Front Panel (First Panel) | First Torso Panel | Inner Front Torso Panel |
| | First Shoulder Portion | Inner Left Front Shoulder Portion |
| | Second Shoulder Portion | Inner Right Front Shoulder Portion |
| Inner Rear Panel (Second Panel) | Second Torso Panel | Inner Rear Panel Torso Panel |
| | Third Shoulder Portion | Inner Left Rear Shoulder Portion |
| | Fourth Shoulder Portion | Inner Right Rear Shoulder Portion |
| Outer Front Panel (Fifth Panel) | Third Torso Panel | Outer Front Torso Panel |
| | Fifth Shoulder Portion | Outer Left Front Shoulder Portion |
| | Sixth Shoulder Portion | Outer Right Front Shoulder Portion |
| Outer Rear Panel (Sixth Panel) | Fourth Torso Panel | Outer Rear Torso Panel |
| | Seventh Shoulder Portion | Outer Left Rear Shoulder Portion |
| | Eighth Shoulder Portion | Outer Right Rear Shoulder Portion |

The opening formed by the left front shoulder portion, left rear shoulder portion and the top (i.e., latitudinal) edge of the left side panel is configured for the left arm to pass through the opening is referred to as the left arm opening. The opening formed by the right front shoulder portion, right rear shoulder portion, and top (i.e., latitudinal) edge of the right side panel is configured for the right arm to pass through the opening is referred to as the right arm opening.

Each panel of the chest binder is wider at the top, tapering to a smaller width at the bottom. Each panel of the inner layer is smaller than the outer layer (i.e., undercut) along the edges that form the arm openings and neck openings such that tension is created between the inner and outer layers when the inner and outer layers are joined. In embodiments, the inner panels are specifically undercut around the edges at the neck opening and arm openings such that the inner panels in those regions are between 0.02%-0.2% smaller than the corresponding outer panels.

The inner and outer panels serve different functions and work independently. The inner panels work as a second skin against the body and the outer panels work ergonomically to create compression that has compressive forces in all directions (also called "360 degree compression") of the wearer. In embodiments, each inner panel is smaller than the corresponding outer panel by a range of 0.02%-0.2% and preferably 0.08%.

In embodiments, the front panels are narrower than the back panels. In embodiments, both the front panels and rear panels are the same shape.

The chest binder of the present invention is assembled by first joining the inner panels together, second joining the outer panels together, and then connecting the inner and outer panels at the neck opening, arm openings and waist openings.

The inner panels (i.e., the inner front panel, the inner rear panel, the inner right side panel, and inner left side panel) are stitched together by using any of a number of stitches known by one of ordinary skill in the art such as a straight stitch, chain stitch, cover stitch or lock stitch. In a preferred embodiment the straight stitch is used to connect the inner panels.

The outer panels (i.e., the outer front panel, the outer rear panel, the outer right side panel, and outer left side panel) are stitched together by using any of a number of stitches known by one of ordinary skill in the art such as a straight stitch, chain stitch, cover stitch or lock stitch. In a preferred embodiment the straight stitch is used to connect the panels.

The inner and outer layers are then connected to each other by stitching along the neck opening, right and left arm openings and the bottom (i.e., waist) opening. In embodiments, the inner and outer panels are connected at the arm openings and the neck opening through the use of understitching, specifically a zigzag stitch.

The understitching is done by the steps of: folding over the end portion of the outer panel layer in the direction of the inner panel layer and folding over the end portion of the inner panel layer in the direction of the outer panel layer (i.e., creating "overlip" portions); folding the inner layer overlip portion over an elastic band placed (i.e., within the cavity created by folding over the inner layer); and connecting the inner and outer panels by stitching the inner layer, elastic, folded over portion of the inner layer and folded over portion of the outer layer together. Use of the elastic band provides structure and security around the seams at the neck and arm openings. Stitching in this manner, i.e., by only stitching the folded over portion of the outer layer and not the outer layer itself, provides the chest binder with a clean seam along the neck and arm openings. Other seams, which do not provide as clean a seam along the neck and arm openings could also be used. In embodiments, the seam is created through the use of one line of stitch, but in other embodiments, these layers can be combined by one of any number of stitches such as a zigzag stitch.

In embodiments, the inner and outer panels are also connected at the bottom opening. One of any number of seam types could be used to join the inner and outer panels at the bottom opening. In embodiments, both the bottom of the inner and outer panels are folded over, creating an overlip portion. The inner and outer panels, and the inner and outer layer overlip portions are then stitched together, preferably using a ⅛ inch double needle cover stitch, though other stitching styles can be used.

Joining the inner and outer panels in this manner permit the inner and outer layers to move independently, serving the two different functions of moving with the body for comfort and compressing the chest, as described above. Specifically, the inner layer sits and moves with the body, while the outer layer enhances compression and structure of the chest.

The four inner panels and four outer panels work together ergonomically to provide 360 degree compression around the chest of the wearer.

In embodiments, the front and left side panels are widest at the top and taper down towards the waist, mimicking the natural body contour. In embodiments, the side panel ranges from 25-35% wider at the top of the panel than the bottom of the panel. In embodiments, the edges of the right and left side panels are curved such that the minimum width of each side panel occurs at a point between the top and bottom of the respective side panel edge.

The side panels are designed to have less longitudinal edge length than the corresponding longitudinal edges of the front and rear panels. When the side panel edges are connected in a way that the top of the side panel is coextensive with the bottom of the arm opening and the bottom of the side panel is coextensive with the bottom of the bottom of the front or rear panel, the corresponding seam length is mismatched. In other words, the side panel edge is stretched (due to the nature of the elastic material of which the side panel is comprised) such that the top of the side panel is coextensive with the bottom of the arm opening and the bottom of the side panel is coextensive with the bottom of the bottom of the front or rear panel. As a result, when the side panel is in a relaxed (i.e., non-stretched state), the corresponding edge of the front or rear panel is contracted, providing a compressive force on the front and rear panels to provide tension on the front and rear panels.

In an exemplary embodiment, the edges of the outer rear panels are 6 1/16 inches and the outer side panel edges configured to join with the outer rear panel edges are 5-11/16 inches. The edges of the outer front panel are 5-13/16 inches and the outer side panel edges configured to join with the outer front panel edges are 5⅜ inches. The corresponding inner panel edges are of smaller dimensions.

In embodiments, the longitudinal edges of the inner and outer side panels are joined with the longitudinal edges of the corresponding inner and outer front and rear panels in a way that there is more tension above a fixed (i.e., anchor) point than below the fixed point, with the fixed point being located below the bust of line of the wearer when the chest binder is worn with the front panels (or rear panel when the chest binder is worn in its 180-degree rotatable embodiment) covering the bust of the wearer.

In embodiments, each of the panels is constructed with a number of notches to facilitate the alignment of the panels when they are joined and to aid in creating the differing stretch and compression zones of the chest binder. In embodiments, notches placed along the edges of the arm, neck and bottom openings are strictly for aiding in the optical alignment of the inner and outer layers when connecting them along the arm, neck and bottom openings. In contrast, the notches placed along the longitudinal edges of the side panels and front and rear panels are strategically positioned such that when the longitudinal notches of the side panels are aligned with the respective longitudinal notches of the longitudinal edges of the front and rear panels, the notches identify a fixed point, operating as an anchor point.

Joining of the panels in this manner creates stretch above and below the anchor point, with the most tension and least stretch located across the chest (i.e., bust area, as opposed to the ribcage) in order to maximize compression. The least tension and most stretch are located at the arm opening on both the left and right sides and at the ribcage to increase comfort. The opposing compressive forces on both sides of the body creates compression inwards, i.e., the location of the side panels, which in turn is offset by the compression from the front and back panels. This provides the appearance of a smooth flattened surface.

One of ordinary skill in the art would recognize that in view of the varying bust configuration of potential wearers, based on factors such as age and bust size, the location of the fixed (i.e., anchor) point and placement of the notches along the longitudinal edges of the side panels and front and rear panels (when used) could vary in order to maintain the placement of the notches at a location below the bust line of the anticipated wearer.

In embodiments, the width of the shoulder portions gradually increases from the high point shoulder to the front and back arm hole and neckline. In a preferred embodiment the shoulder width gradually increases between 40-60%. This increased width of the shoulder portions functions to distribute weight and ease tension on the high point shoulder.

The front and back shoulder portions are designed to connect to form two shoulder straps with the high point shoulder on the straps (i.e., the traditional focal location of the weight bearing forces of the chest binder) placed behind the shoulder, rather than the top of the shoulder, thus distributing the weight of the wearer's breast tissue around the body instead of on the shoulder blade, as would be the case with a conventional brassiere. As a result of the high point shoulder placement, the straps are not weight bearing and so have minimal pressure on the shoulder slope and neckline for maximum comfort. The utility of the panels accentuates this aspect of the design so that all weight and compression is dealt with below the shoulder point. This design is in contrast to a conventional sports bra wherein the shoulder straps act as an anchor in order to lift the breast tissue, with the pressure mounting on the shoulder slope.

In embodiments, each arm opening formed by the connecting of the shoulder portions has been scooped out to define a shape that accommodates varying body types comfortably while at the same time accentuating the function of compression by smoothing out any ripple lines across the chest.

In embodiments, one or more line stitches extends around the circumference of the chest binder at the lower portion of the outer front, side and back panels to connect the inner and outer panels at the bottom opening. In a preferred embodiment, two closely spaced line stitches are used. In a preferred embodiment, a ⅛ inch double needle cover stitch is used. The line stitches join the outer panels and inner panels and form a band (i.e., a hem) at the bottom of the panels of the chest binder, defined by the area below this line stitching and extending to the bottom opening. The location of the band is decided based on a number of factors including torso length and bust size.

In embodiments, the chest binder is designed to be 180-degree rotatable such that the front panels function as rear panels and the rear panels function as front panels. In a preferred embodiment, the front panels and rear panels are designed with differing necklines to increase the versatility of the chest binder. In one embodiment, the front panels are designed with a scoop neck (lower neck) neckline and the rear panels are designed with a V-neck (higher neck) neckline. Both designs provide the maximum level of compression. When rotated, the high point shoulder on the straps shifts to in front of the midpoint line, still remaining off of the top of the shoulder and distributing the weight away from the neck and shoulder area.

The chest binder can be fabricated out of one of a number of different fabrics having the appropriate compression and/or elasticity, such as, 32%-38% elastane and the like.

Fabric such as 32%-38% elastane, has a grain that one of ordinary skill in the art will recognize affects the properties of the fabric. For example, the fabric stretches more in the crossgrain direction. Alternatively, when the fabric is cut with a bias on the grain line, it is less stable. In embodiments, the panel fabric of one or more panels is cut on the crossgrain, allowing for 360-degree stretch around the circumference of the wearer's body. In a preferred embodiment, each of the panels for the inner and outer layers is cut on the crossgrain.

In an embodiment, elastic manufactured by Fulflex, preferably between (¼ inch and ½ inch) is used around the neckline and arm openings to optimize performance, comfort and streamlines the shape of design.

In embodiments, the inner seams that are sewn along the neckline and armholes of the inner layer and elastic of chest binder are tucked under to sit against the body and to keep the material flat against the body. In a preferred embodiment, a zigzag stitch is used.

These and other features of this invention are described in, or are apparent from, the following detailed description of various exemplary embodiments of this invention.

BRIEF DESCRIPTION OF THE DRAWINGS

Exemplary embodiments of this invention will be described with reference to the accompanying figures wherein.

DETAILED DESCRIPTION OF THE EXEMPLARY EMBODIMENTS

Figure 1:
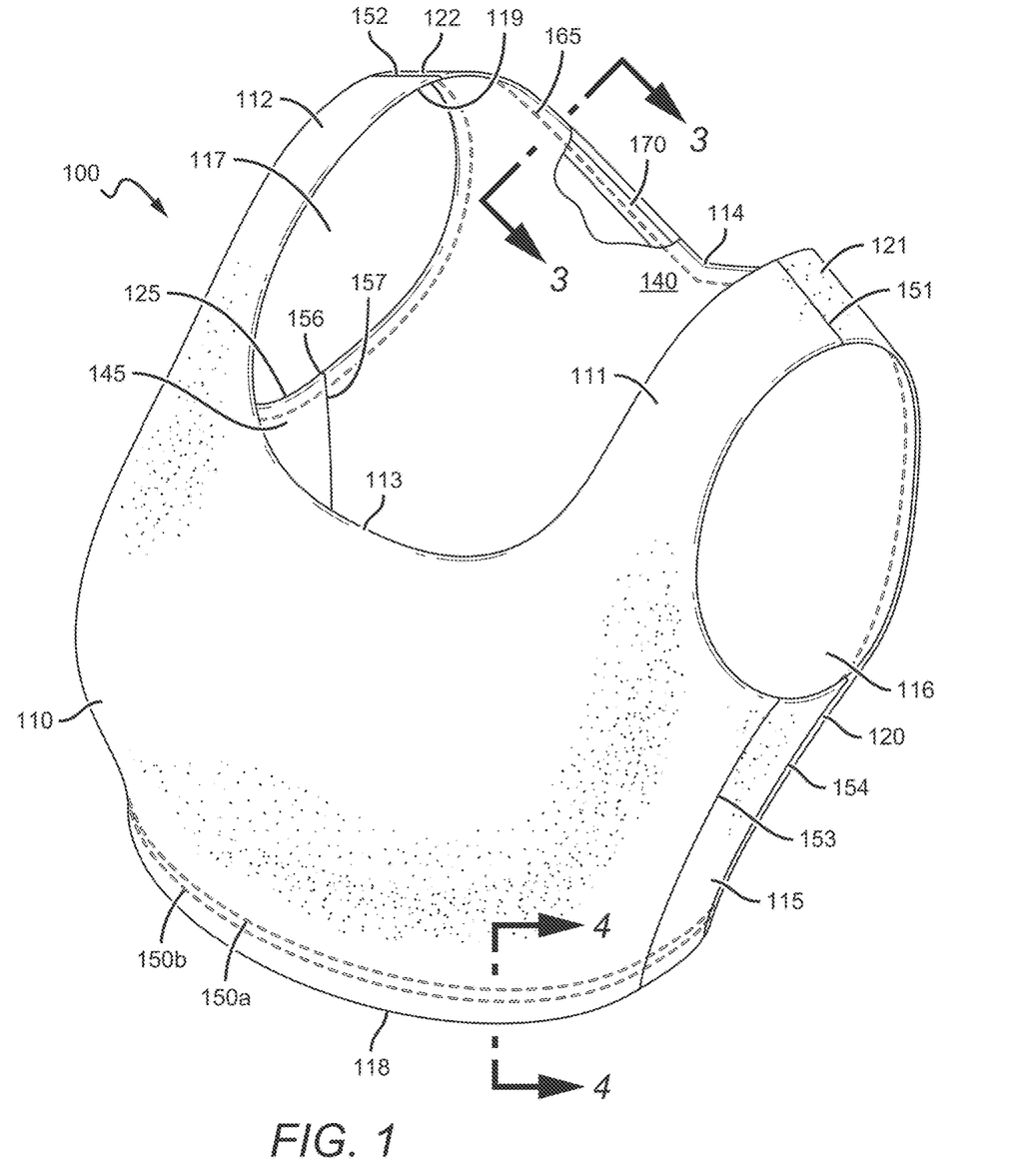
FIG. 1 is a front perspective view of the chest binder of the present invention.

With reference to FIG. 1, the details of the construction of chest binder 100 are illustrated. The chest binder of the present invention, shown its fully assembled state, consists of an outer layer of interconnected panels and an inner layer of interconnected panels. The outer layer of panels comprises outer front panel (i.e., fifth panel) 110, outer left side panel (i.e., seventh panel) 115, outer rear panel (i.e., sixth panel) 120, and outer right side panel (i.e., eighth panel) 125. The inner layer of panels comprises the inner front panel (i.e., first panel, not shown), inner left side panel (i.e., third panel, not shown), inner rear panel (i.e., second panel) 140 and inner right side panel (i.e., fourth panel) 145. The outer and inner panels are joined at the neck opening (which comprises scoop neck 113 and V-neck 114), left arm opening 116, right arm opening 117 and bottom opening 118.

Turning to the outer layer of construction, outer front panel 110, comprises an outer front torso panel, outer left front shoulder portion 111 and outer right front shoulder portion 112 configured to extend over the left and right shoulders of the wearer. The left and right shoulder portions are spaced from each other and extend from the torso panel to define a portion of the neck opening.

Outer left front shoulder portion 111 of outer front panel 110 is joined to the outer left rear shoulder portion 121 of outer rear panel 120 along seam (i.e., third shoulder seam) 151. Outer right front shoulder portion 112 of outer front panel 110 is joined to the outer right rear shoulder portion 122 of outer rear panel 120 along seam (i.e., fourth shoulder seam) 152.

The shoulder seams, including shoulder seams 151 and 152 and the first and second shoulder seams joining the left and right shoulder portions of the inner front and inner rear panels are located behind the top of the shoulder at the high point shoulder (i.e., the traditional focal location of the weight bearing forces of the chest binder), rather than the top of the shoulder. The construction of the chest binder is such that the weight distribution of the wearer's breast tissue is distributed around the body instead of on the shoulder blade, as would be the case with a conventional brassiere.

Outer left side panel 115 is joined at the first longitudinal edge to the outer front torso panel of outer front panel 110 along seam 153. Outer left side panel 115 is joined at the second longitudinal edge to the outer rear torso panel of outer rear panel 120 along seam 154. Similarly, outer right side panel 125 is joined at the first longitudinal edge to the outer front torso panel of outer front panel 110 along seam 155 (not shown). Outer right side panel 125 is joined at the second longitudinal edge to the outer rear torso panel of outer rear panel 120 along seam 156.

The corresponding inner panels, (inner front panel, inner left side panel, inner rear panel and inner right side panel) of which only inner rear panel 140 and inner right side panel 145 can be seen in FIG. 1, are similarly interconnected to form the inner layer of the chest binder. The only seam visible joining the panels of the inner layer in the perspective view of FIG. 1 is seam 157, joining inner right side panel 145 with inner rear torso panel of inner rear panel 140.

Outer front panel 110 (and the inner front panel) is designed with scoop neck 113 and outer rear panel 120 (and inner rear panel 140) is designed with V-neck 114. Scoop neck 113 and V-neck 114 form the neck opening. Chest binder 100 is 180-degree rotatable depending on the neckline the wearer desires. When chest binder 100 is rotated so that V-neck 114 is at the front of the wearer, outer rear panel 120 acts as the outer front panel and the outer front panel 110 acts as the outer rear panel.

The upper portion of inner rear panel 140 is joined to the upper portion of outer rear panel 120, and the upper portion of the inner front panel (not shown) is joined to the upper portion of outer front panel 110 at the neck opening by seam 165, which travels along the neck opening, specifically V-neck 114 and scoop neck 113. Seam 165 connects these panels by use of an anchored understitch so that the inner and outer layers can move independently.

The understitching is done by folding over the end portion of the outer panel layer in the direction of the inner panel layer and folding over the end portion of the inner panel layer in the direction of the outer panel layer (i.e., creating an "overlip" portion) and placing elastic band 170 within the cavity created by folding over the inner layer, and then connecting the inner and outer panels by stitching the inner layer, elastic, folded over portion of the inner layer and folded over portion of the outer layer together. Details of this stitch are discussed in more detail in the discussion of FIG. 3. In embodiments, the inner panel, the overlip of the inner panel, the elastic, and overlip of the outer panel are sewn together through the use of one line of stitch, as shown in seam 165, but in other embodiments other stitch types such as a zigzag stitch may be used.

The same understitching used at the neck opening is also used around the perimeter of left arm opening 116 and right arm opening 117 to join the inner and outer layers of the chest binder.

Figure 4:
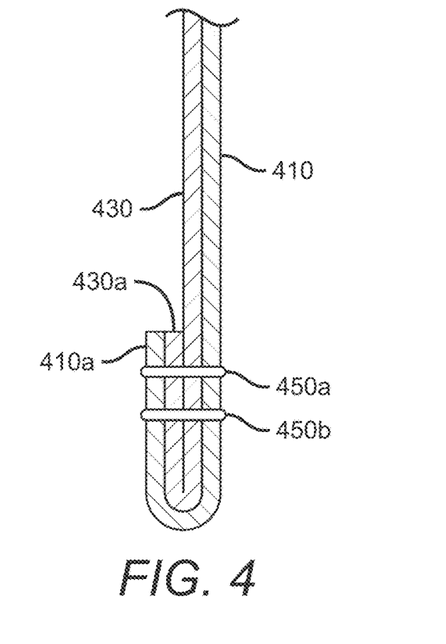
FIG. 4 is a cross-sectional view of the chest binder taken along the lines 4-4 in FIG. 1 in the direction shown by the arrows.

In addition to being joined along the neck opening, left arm opening and right arm opening, the inner and outer layers of the chest binder of the present invention are also joined along the bottom opening. In the embodiment shown in FIG. 1, the inner and outer layers are connected at bottom opening 118 through the use of a double stitch comprising stitches 150*a* and 150*b* to form the seam at the bottom opening. Details on this seam are shown in FIG. 4. Two line stitches (seam 150, comprising line stitch 150*a* and line stitch 150*b*) are shown around the circumference of the chest binder at the lower portion of the outer front, side and back panels. The line stitches 150*a* and 150*b* join the outer panels and inner panels (as shown in the detail on FIG. 4). Joining the inner layer and outer layer of the chest binder at neck opening 113, right arm opening, left arm opening, and bottom opening only, permits the inner and outer layers of the chest binder to move independently, serving the two different functions of moving with the body for comfort while also compressing the chest.

Figure 2:
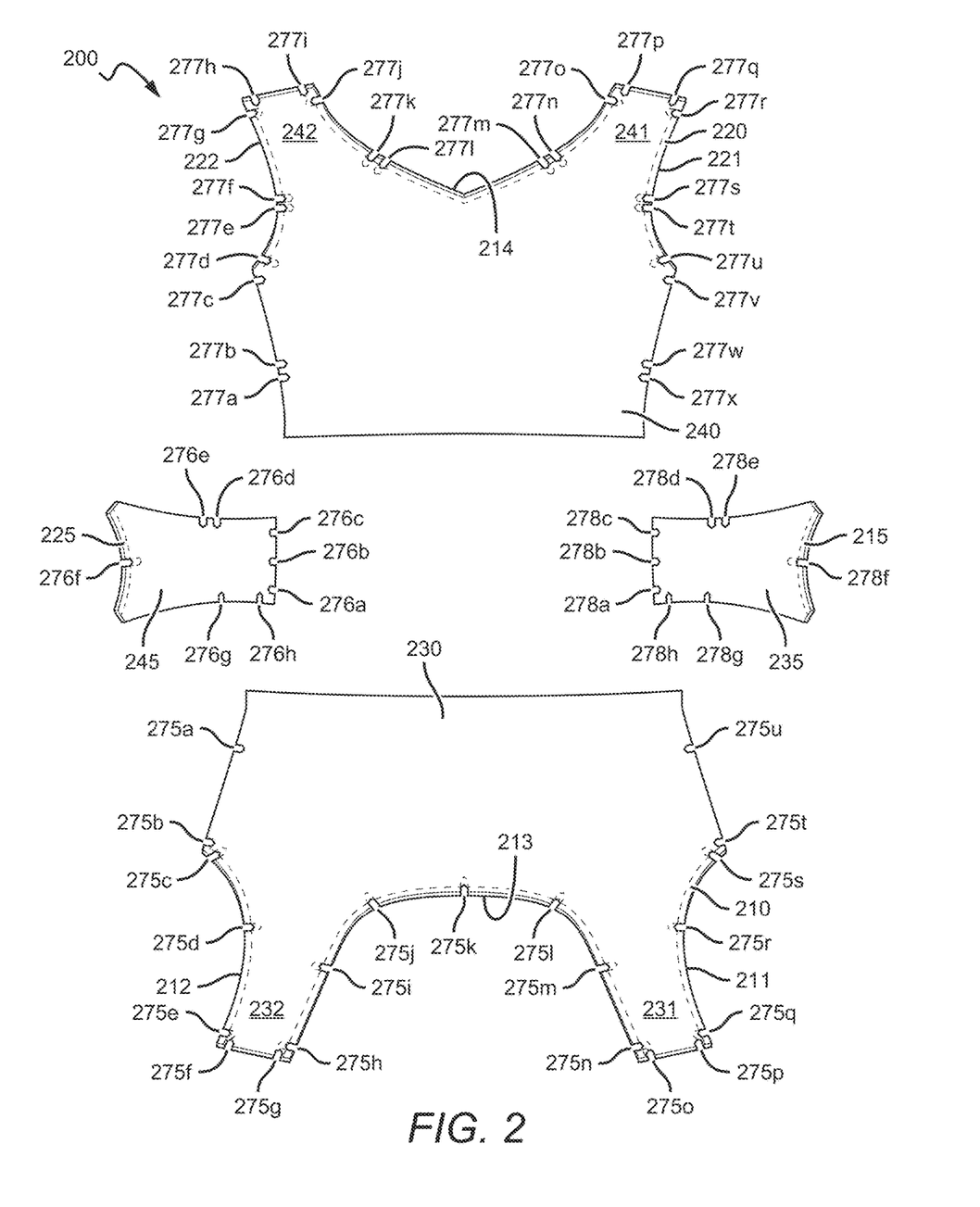
FIG. 2 is an exploded view of the chest binder of the present invention.

Turning to FIG. 2, an exploded view of the chest binder is shown showing the inner and outer panels prior to being joined to form the inner and outer layers of the chest binder. Outer front panel 210, outer left side panel 215, outer rear panel 220 and outer right side panel 225 are each shown with their corresponding inner panels, namely inner front panel 230, inner left side panel 235, inner rear panel 240 and inner left side panel 245. The outer panels can be joined together by one of a number of means, including stitching, fabric glue, or seam welding. The inner panels can be joined in a similar manner.

As shown in FIG. 2, the inner panels are coextensive with the outer panels except along the portions of the inner and outer panels that form the neck opening (along scoop neck 213 and V-neck 214) and the left arm opening and right arm opening. In embodiments (not shown), inner front panel 230 does not include inner left front shoulder portion 231 and inner right front shoulder portion 232. Similarly, in embodiments (not shown) the inner rear panel does not include inner left rear shoulder portion 241 and inner right rear shoulder portion 242.

In embodiments, the inner and outer panels each contain notches to serve two functions: (a) aid the optical alignment of the inner and outer panels when they are being joined at the neck opening, left and right arm openings and bottom opening, and (b) aid in the creation of a mismatched seam of two differing zones of stretch and compression along the longitudinal edges of the side panels and corresponding longitudinal edges of the torso panels of the inner and outer front and back panels (i.e., along the side panel seams).

In embodiments, the alignment of the inner and outer panels and the creation of the mismatched seam is effectuated without the use of notches.

As shown in FIG. 2, the inner and outer front panels contain notches 275a-275u, the inner and outer left side panels contain notches 278a-278h, the inner and outer right side panels each contain notches 276a-276h, and the inner and outer rear panels contain notches 277a-277x.

Notches 275b-275t, 276a-276c, 276f, 276h, 277c-277v and 278a-278c, 278f, 278h are used for optical alignment. Notches 278d, 278e, 278g, 277w, 277x, 277a, 277b, 276d, 276e, 276g, 275u and 275a are used to help create the mismatched seam. In the embodiment shown in FIG. 2, the rear panels are shown with pairs of notches, 277a and 277b, 277e and 277f, 277s and 277t, 277w and 277x to help distinguish the rear panel from the front panel. Similarly, the edges of the side panels that join with the rear panels have double notches (notches 276d and 276e, 278d and 278e) in order to aid the manufacturer of the chest binder in properly joining the panels together. While these double notches have been chosen in this embodiment to differentiate the rear panels from the front panels, any other configuration of notches can be used for optical alignment.

Figure 5:
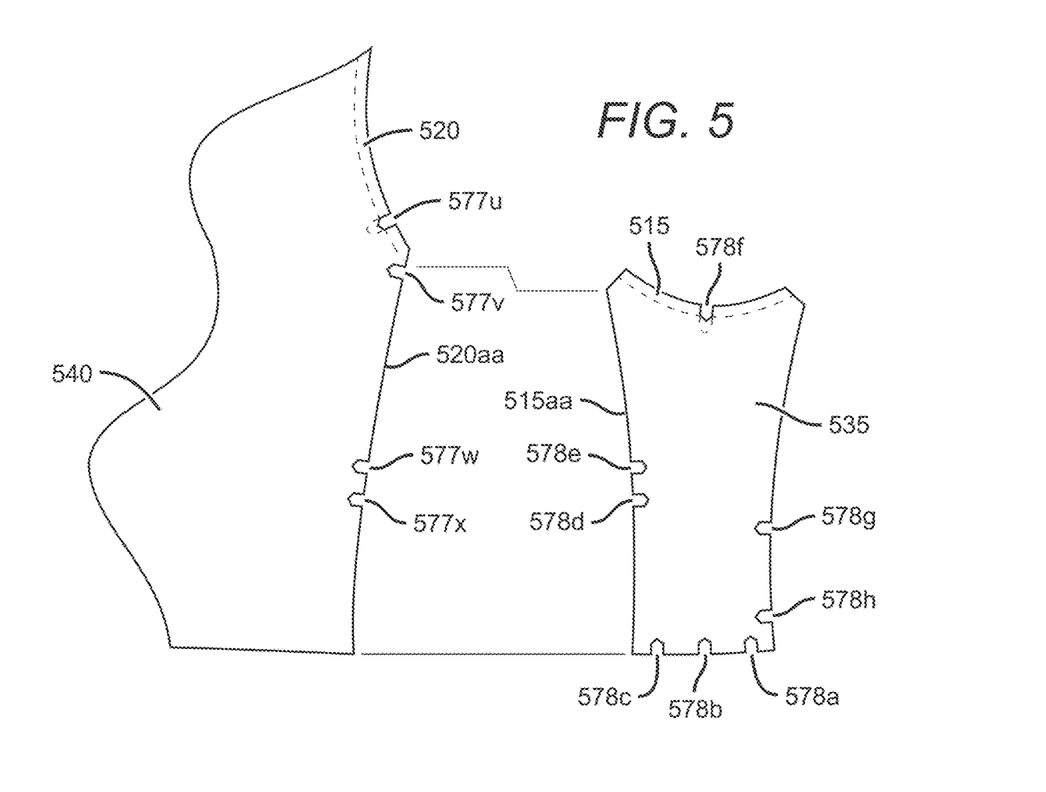
FIG. 5 is a front view of left side panel and a portion of the right side of the rear panel of the present invention shown in an unjoined state.

The location of the notches along the edge of the panels, namely notches 275a, 275u, 278d, 278e, 278g, 277w, 277x, 277a, 277b, 276d, 276e, and 276g, located at a fixed point below the bust line of the wearer when the chest binder is worn with the corresponding panel covering the bust of the wearer, is important as each of these notches operates as an anchor point of the corresponding mismatched seam, creating stretch above and below the anchor point, when the panels are joined, with the most tension and least stretch located across the chest in order to maximize compression. FIG. 5 addresses the details on this mismatched seam configuration.

As seen in FIG. 2, the inner panels, along the neck opening, left arm opening and right arm opening are designed to be of a smaller dimension than the corresponding outer panels. In the embodiment shown in FIG. 2, the inner panels are designed to be approximately 0.08% smaller than the corresponding outer panels. However, the inner panels range from 0.02%-0.2% smaller than the outer panel.

As seen in FIG. 2, the left side panel (comprising outer left side panel 215 and inner left side panel 235) is wider at the top and tapers as it reaches the bottom of the chest binder. In the embodiment shown in FIG. 2, the left side panel is approximately 25%-35% wider at the top of the side panel than it is at the bottom of the side panel. The right side panel is of similar dimensions.

Figure 3:
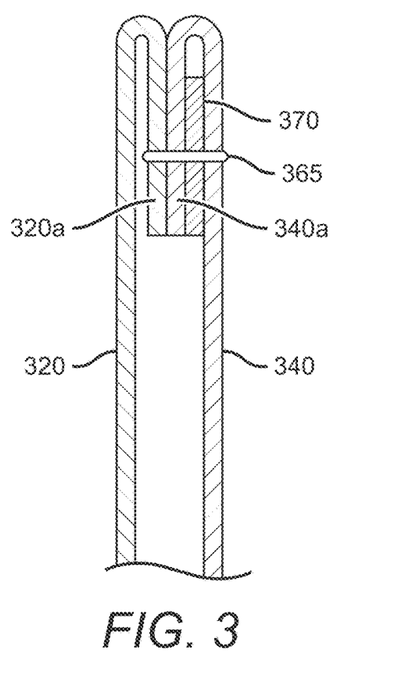
FIG. 3 is a cross-sectional view of the chest binder taken along the lines 3-3 in FIG. 1 in the direction shown by the arrows.

Turning to FIG. 3, a cross-sectional view of the chest binder is illustrated, taken along the lines 3-3 in FIG. 1 in the direction shown by the arrows.

To create the understitch illustrated in FIG. 3, end portion 320a of outer rear panel 320 is folded over inward in the direction of the inner rear panel (creating an overlip portion) so that it adjoins end portion 340a of inner rear panel 340, which is similarly folded over in the direction of the outer panel 320 to create an overlip portion. End portion 340a of inner rear panel is folded over elastic band 370, which is located within the cavity formed by the folded over inner rear panel. Seam 365 passes through inner panel 340, elastic band 370, end portion 340a, and end portion 320a to join the inner and outer layers of the chest binder. Though shown specifically with respect to the joining of the inner and outer rear panels in FIG. 3, this understitch configuration is used throughout the perimeter of the neck opening (with reference to FIG. 1, neck opening 119, along V-neck 114, scoop neck 113, and the perimeter of left arm opening 116 and right arm opening 117), connecting the various outer and inner layers that form these openings. Use of elastic band 370 provides structure and security around seam 365 at the neck and arm openings. Stitching in this manner (where seam 365 does not pass through outer layer 320) provides the chest binder with a clean seam along the neck and arm openings.

Other seams, which do not provide as clean a seam along the neck and arm openings could also be used. In the embodiment shown in FIG. 3, seam 365 is created through the use of one line of stitch, but in other embodiments (not shown), these layers can be combined by one of any number of stitches such as a zigzag stitch.

Turning to FIG. 4, a cross-sectional view of the chest binder is illustrated, taken along the lines 4-4 in FIG. 1 in the direction shown by the arrows. FIG. 4 illustrates the two line stitches used to attach the outer and inner panels along the perimeter of the bottom opening (bottom opening 118 in FIG. 1). In the embodiment shown in FIG. 4, line stitches 450a and 450b are shown. In embodiments (not shown), only one line stitch is used. As shown in FIG. 4, the bottom ends of the outer panel (outer front panel 410) and inner panel (inner front panel 430) are folded over, so that the end of inner front panel 430a and inner front panel 430 are both sandwiched between the end of outer front panel 410a and outer front panel 410 as show in FIG. 4. Line stiches 450a and 450b each pass through the end of outer front panel 410a, end of inner front panel 430a, inner front panel 430 and outer front panel 410 to form seam 450 and join the panels. This seam is carried through the perimeter of the bottom opening (bottom opening 118 in FIG. 1).

Turning to FIG. 5, a front view of the left side panel and a portion of the right side of the rear panel is shown before the panels are joined together, similar to the illustration in FIG. 2 (but in a non-exploded view). Specifically, outer rear panel 520, inner rear panel 540, outer left side panel 515 and inner left side panel 535 are shown deconstructed. The inner panels are coextensive with the corresponding outer panels, except they are both shorter along the portions shown which comprise the left arm opening. Inner and outer panel notches 577u through 577x, and left side panel notches 578a through 578h are also shown.

As seen in FIG. 5, the left side panel edge is shorter than the left edge (the visible edge in FIG. 5) of the rear panel. The inner and outer side panels are joined with the inner and outer front panels and inner and outer rear panels in a similar fashion and will be discussed herein with reference to the outer left side panel and outer rear panel, with the understanding that the inner and outer panels will be similarly joined together.

As shown in FIG. 5, left side panel edge 515aa (i.e., the second longitudinal edge of outer left side panel 515) is to be joined with outer rear panel edge 520aa. Both left side panel edge 515aa and rear panel edge 520aa are placed side-by-side. After taking into account the angular shape of the edges and the respective overall length of the edges, left side panel edge 515aa is shorter than rear panel edge 520aa when in a relaxed state.

In order to make the edges coextensive to create the required seam for the inner or outer panels, left side panel edge 515aa is stretched (possible because of the elastic nature of the fabric used to construct the inner and outer layers) so that the top of left side panel edge 515aa aligns with the top of rear panel edge 520aa and the bottom of left side panel edge 515aa aligns with the bottom of rear side panel edge 520aa. While stretching left side panel edge 515aa, to attain this alignment, notches 578e and 578d of left side panel edge 515aa are kept in alignment with notches 577w and 577x respectively of rear panel 520. When the side panel is in a relaxed (i.e., non-stretched state), edge 520aa of the rear panel is contracted, providing a compressive force on the front and rear panels to provide tension on the front and rear panels.

The placement of notches 578e, 578d and 577w and 577x, operate as anchor points, strategically placed at a fixed point an area below the bust area of the wearer when the chest binder is worn in a position where the rear panels cover the bust area. The notches create stretch above and below the anchor points (i.e., fixed points), with the most tension and least stretch located across the chest (i.e., bust area, as opposed to the rib cage) above the anchor points in order to maximize compression and less tension and most stretch located below anchor points. The least tension and most stretch are located at the arm opening on both the left and right sides and at the ribcage to increase comfort.

While notches 578d, 578e, 577w, 577x, are present in the embodiment shown in FIG. 5, notches are not necessary to construct the chest binder of the present invention to align the various panels and identify the fixed point (i.e., anchor point) necessary to create the differing zones of stretch and compression along the longitudinal edges of the side panels and corresponding longitudinal edges of the torso panels of the inner and outer front and back panels (i.e., along the side panel seams).

Now that embodiments of the present invention have been shown and described in detail, various modifications and improvements thereon will become readily apparent to those skilled in the art. Accordingly, the exemplary embodiments of the invention, as set forth above, are intended to be illustrative, not limiting. The spirit and scope of the present invention is to be construed broadly.

What is claimed is:

1. A chest binder comprising:
   an inner layer and an outer layer joined at a neck opening, a first arm opening, a second arm opening and a bottom opening;
   the inner layer comprising:
      a first panel comprising a first torso panel with longitudinal edges, a first shoulder portion, and a second shoulder portion, wherein the first shoulder portion and the second shoulder portion are spaced from each other and extend from the first torso panel to define at least a portion of the neck opening;
      a second panel comprising a second torso panel with longitudinal edges, a third shoulder portion, and a fourth shoulder portion, wherein the third shoulder portion and the fourth shoulder portion are spaced from each other and extend from the second torso panel to define at least a portion of the neck opening;
      third and fourth panels each having first and second longitudinal edges;
         the first longitudinal edges of the third and fourth panels joined to the longitudinal edges of the first torso panel;
         the second longitudinal edges of the third and fourth panels joined to the longitudinal edges of the second torso panel;
         the first shoulder portion joined to the third shoulder portion at a first shoulder seam, and the second shoulder portion joined to the fourth shoulder portion at a second shoulder seam; and
   the outer layer comprising:
      a fifth panel comprising a third torso panel with longitudinal edges, a fifth shoulder portion, and a sixth shoulder portion, wherein the fifth shoulder portion and the sixth shoulder portion are spaced from each other and extend from the third torso panel to define at least a portion of the neck opening;
      a sixth panel comprising a fourth torso panel with longitudinal edges, a seventh shoulder portion, and an eighth shoulder portion, wherein the seventh shoulder portion and the eighth shoulder portion are spaced from each other and extend from the sixth panel to define at least a portion of the neck opening;
      seventh and eighth panels each having first and second longitudinal edges;
         the first longitudinal edges of the seventh and eighth panels joined to the longitudinal edges of the third torso panel;
         the second longitudinal edges of the seventh and eighth panels joined to the longitudinal edges of the fourth torso panel;
         the fifth shoulder portion joined to the seventh shoulder portion at a third shoulder seam, and the sixth shoulder portion joined to the eighth shoulder portion at a fourth shoulder seam.

2. The chest binder of claim 1 wherein:
   the inner and outer panels are made of an elastic material;
   the first longitudinal edges of the third and fourth panels are shorter than the longitudinal edges of the first torso panel when the first torso panel, third panel and fourth panel are all in a relaxed state;
   the first longitudinal edges of the seventh and eighth panels are shorter than the longitudinal edges of the third torso panel when the third torso panel, seventh panel and eighth panel are all in a relaxed state;
   the first longitudinal edges of the third and fourth panels are joined to the longitudinal edges of first torso panel with the first longitudinal edges of the third and fourth panels in a stretched state such that the first longitudinal edges of the third and fourth panels are coextensive with the longitudinal edges of the first torso panel and there is more tension above a fixed point than below the fixed point, the fixed point being located below the bust line of the wearer when the chest binder is worn with the second and fourth torso panels covering the bust of the wearer; and
   the first longitudinal edges of the seventh and eighth panels are joined to the longitudinal edges of the third torso panel with the first longitudinal edges of the seventh and eighth panels in a stretched state such that the first longitudinal edges of the seventh and eighth panels are coextensive with the longitudinal edges of the third torso panel and there is more tension above the fixed point than below the fixed point.

3. The chest binder of claim 2 wherein:
   the first and second longitudinal edges of the third, fourth, seventh and eighth panels are curved such the minimum width of each of the third, fourth, seventh and eighth panels occurs at a point between the top and bottom of each of the longitudinal edges.

4. The chest binder of claim 2 wherein:
   the second longitudinal edges of the third and fourth panels are shorter than the longitudinal edges of the second torso panel when the second torso panel, third panel and fourth panel are all in a relaxed state;
   the second longitudinal edges of the seventh and eighth panels are shorter than the longitudinal edges of the fourth torso panel when the fourth torso panel, seventh panel and eighth panel are all in a relaxed state;

the second longitudinal edges of the third and fourth panels are joined to the longitudinal edges of the second torso panel with the second longitudinal edges of the third and fourth panels in a stretched state such that the second longitudinal edges of the third and fourth panels are coextensive with the longitudinal edges of the second torso panel and there is more tension above a fixed point than below the fixed point, the fixed point being located below the bust line of the wearer when the chest binder is worn with the second and fourth torso panels covering the bust of the wearer; and the second longitudinal edges of the seventh and eighth panels are joined to the longitudinal edges of the fourth torso panel with the second longitudinal edges of the seventh and eighth panels in a stretched state such that the second longitudinal edges of the seventh and eighth panels are coextensive with the longitudinal edges of the fourth torso panel and there is more tension above the fixed point than below the fixed point.

5. The chest binder of claim 1, wherein:

the outer layer and inner layer of the chest binder are joined at the neck opening and arm openings by:
  folding a portion of the outer layer along the neck opening in the direction of the inner layer;
  folding a portion of the inner layer along the neck opening in the direction of the outer layer over an elastic band; and
  stitching together the folded over portion of the outer layer, folded over portion of the inner layer, the elastic band and the inner layer;

the outer layer and inner layer of the chest binder are joined at the bottom opening by:
  folding a portion of the inner layer along the bottom opening in the direction away from the outer layer;
  folding a portion of the outer layer along the bottom opening over the folded portion of the inner layer; and
  stitching together the folded over portions of the outer layer and inner layer, and the outer layer and inner layer.

6. The chest binder of claim 1 wherein the shoulder seams are configured to be located behind the top of the shoulder of the wearer.

7. The chest binder of claim 1 wherein the first, second, third and fourth panels are between 0.02% to 0.2% smaller in size than the fifth, sixth, seventh and eighth panels.

8. The chest binder of claim 7 wherein the third, fourth, seventh and eighth panels are 25% to 35% wider along the edge that forms the arm opening than the edge that forms the bottom opening.

9. The chest binder of claim 8 wherein:
  the inner and outer layers are fabricated using a fabric which stretches more in the crossgrain direction than in the lengthwise grain direction; and
  wherein the fabric for at least one of the first, second, third, fourth, fifth, sixth, seventh, or eighth panels is cut on the crossgrain direction.

10. The chest binder of claim 9 wherein each of the first, second, third, fourth, fifth, sixth, seventh, or eighth panels is cut on the crossgrain direction.

\* \* \* \* \*